(12) United States Patent
Zhang

(10) Patent No.: US 10,022,476 B2
(45) Date of Patent: Jul. 17, 2018

(54) DRUG RELEASING MEDICAL CATHETERS, TUBES, AND DEVICES

(71) Applicant: Medcatheters, Inc., Wilmington, DE (US)

(72) Inventor: Jie Zhang, Salt Lake City, UT (US)

(73) Assignee: Medcatheters, Inc., Wilmington, DE (US)

( * ) Notice: Subject to any disclaimer, the term of this patent is extended or adjusted under 35 U.S.C. 154(b) by 151 days.

(21) Appl. No.: 15/063,959

(22) Filed: Mar. 8, 2016

(65) Prior Publication Data

US 2016/0184485 A1 Jun. 30, 2016

Related U.S. Application Data

(63) Continuation of application No. 13/638,577, filed as application No. PCT/US2011/030563 on Mar. 30, 2011, now Pat. No. 9,308,298.

(60) Provisional application No. 61/318,881, filed on Mar. 30, 2010.

(51) Int. Cl.
*A61L 29/16* (2006.01)
*A61M 19/00* (2006.01)
*A61M 25/00* (2006.01)

(52) U.S. Cl.
CPC ............ *A61L 29/16* (2013.01); *A61M 19/00* (2013.01); *A61M 25/00* (2013.01); *A61M 25/002* (2013.01); *A61M 25/0009* (2013.01); *A61M 25/0045* (2013.01); *A61L 2300/402* (2013.01); *A61L 2300/404* (2013.01); *A61L 2300/602* (2013.01); *A61L 2420/02* (2013.01); *A61M 2025/0057* (2013.01)

(58) Field of Classification Search
CPC .......... A61M 19/00; A61M 2025/0057; A61M 25/00; A61M 25/0009; A61M 25/002; A61M 25/0045; A61L 2300/402; A61L 2300/404; A61L 2300/602; A61L 2420/02; A61L 29/16
See application file for complete search history.

(56) References Cited

U.S. PATENT DOCUMENTS

| 4,917,686 | A | * | 4/1990 | Bayston | ................. A61L 27/54 604/265 |
|---|---|---|---|---|---|
| 5,304,121 | A | * | 4/1994 | Sahatjian | ................. A61F 2/90 604/509 |
| 5,417,671 | A | | 5/1995 | Jackson | |
| 5,562,652 | A | | 10/1996 | Davis | |
| 5,616,119 | A | | 4/1997 | Davis | |

(Continued)

OTHER PUBLICATIONS

International Search Report and Written Opinion dated Dec. 22, 2011 for PCT/US2011/030563, Applicant Sparkmed Research, LLC et al.

*Primary Examiner* — Quynh-Nhu H Vu
(74) *Attorney, Agent, or Firm* — Thorpe North & Western, LLP

(57) ABSTRACT

The present disclosure relates to medical catheters, tubes, and other medical devices, systems, and methods. The catheter, tube, or other medical device is capable of releasing drugs for extended periods of time. Drugs can be loaded into the wall thereof with a loading solution. The drug in the wall of the device and in the loading solution can be in dynamic equilibrium, yielding stable and easy-to-manufacture products.

36 Claims, 2 Drawing Sheets

(56) References Cited

U.S. PATENT DOCUMENTS

| | | | |
|---|---|---|---|
| 5,624,704 A * | 4/1997 | Darouiche | A61L 27/54 |
| | | | 427/2.24 |
| 2003/0032942 A1 * | 2/2003 | Theeuwes | A61M 25/00 |
| | | | 604/537 |
| 2004/0220511 A1 | 11/2004 | Scott et al. | |
| 2005/0238733 A1 | 10/2005 | Henry | |
| 2006/0074388 A1 | 4/2006 | Dextradeur et al. | |
| 2007/0059348 A1 | 3/2007 | Friis et al. | |
| 2007/0161967 A1 | 7/2007 | Fischer, Jr. et al. | |
| 2007/0161968 A1 | 7/2007 | Fischer, Jr. et al. | |
| 2008/0241245 A1 * | 10/2008 | Myers | A61K 9/0019 |
| | | | 424/484 |

\* cited by examiner

DRUG RELEASING MEDICAL CATHETERS, TUBES, AND DEVICES

The present application is a continuation of U.S. patent application Ser. No. 13/638,577, filed on Apr. 23, 2013, which is a National Stage Application of PCT/US11/30563, filed on Mar. 30, 2011, which claims the benefit of U.S. Provisional Patent Application No. 61/318,881, filed on Mar. 30, 2010, each of which is incorporated herein by reference.

BACKGROUND

Medical catheters, drainage tubes such as urinary (Foley) catheters, and other tubes such as tracheal tubes and central venous catheters, are often used on sensitive mucosal or wound surfaces and can cause pain, discomfort, and/or infection. For example, a Foley catheter, which is a soft, thin rubber tube with a balloon at one end to hold it in place within the bladder, is often used to drain urine from the bladder. It can remain in place for a short or long period of time, and is inserted through the urinary duct (urethra) and into the bladder. As a Foley catheter is used typically when normal urination is disrupted by infection, a swollen prostate gland, bladder stones, injury, or the like, the insertion and use of this device in this already sensitive area can be uncomfortable or become a foreign surface on which biofilm or other microbes can grow. Biofilm in particular, in which bacteria can hide, can form on the surfaces of the catheters, tubes, and other medical devices that are in contact with mammalian mucosa, wound, or other tissues for longer than a few days. Thus, long term use of Foley catheter is often associated with infection in the urinary tract. Furthermore, the use of central venous catheters sometimes causes dangerous infections. As a result of this and other shortcomings, there is a need to provide medical devices and methods of using them with a decreased degree of discomfort and/or decreased possibility of infections.

DETAILED DESCRIPTION

Figure 1:
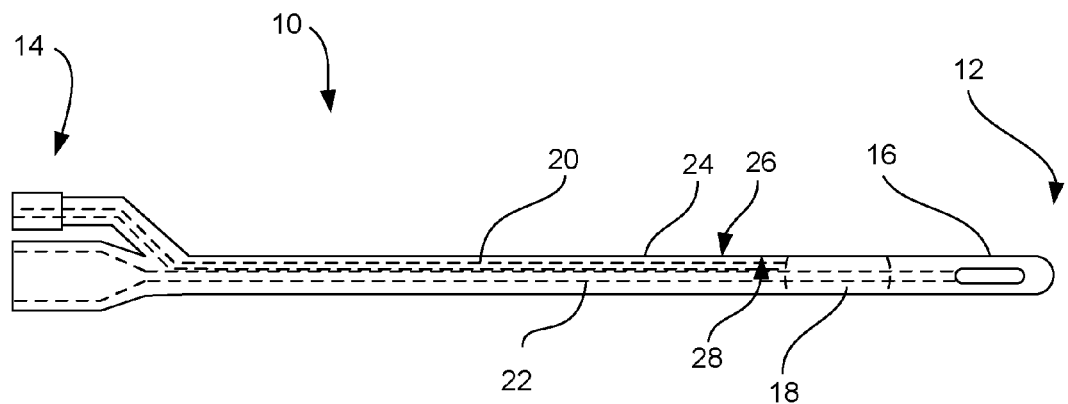
FIG. 1 is a schematic drawing of a urinary (Foley) catheter which can be used in accordance with embodiments of the present disclosure.

Reference will now be made to the exemplary embodiments and specific language will be used herein to describe the same. It will nevertheless be understood that no limitation of the scope of the disclosure is thereby intended. Alterations and further modifications of the inventive features illustrated herein, and additional applications of the principles of the disclosure as illustrated herein, which would occur to one skilled in the relevant art and having possession of this disclosure, are to be considered within the scope of the disclosure. It is also to be understood that this disclosure is not limited to the particular configurations, process steps and materials disclosed herein as these may vary to some degree. Further, it is to be understood that the terminology used herein is used for the purpose of describing particular embodiments only, and is not intended to be limiting as the scope of the present disclosure.

It is noted that, as used in this specification and the appended claims, singular forms of "a," "an," and "the" include plural referents unless the content clearly dictates otherwise.

"Medical catheter," "medical tube," "catheter," and "tube" are used interchangeably and are defined as any catheter or tube used for medical purposes in humans or other mammals. These catheters and tubes include, without limitation, urinary tract catheters (Foley catheter), drainage tubes, feeding tubes, trachea tubes, intravenous catheters, central venous catheters, arterial catheters, umbilical (arterial and venous) catheters, gastric tubes, uterine tubes, chest tubes, peritoneal catheters, renal catheters, dialysis catheters, tissue drainage tubes, or any medical catheter or tube that, when in use, has a surface in contact with mammalian mucosa, wound, or other tissue not protected by skin.

"Foley catheter" and "urinary catheter" are used interchangeably.

"Drug" or "drugs" are substances that can be used to treat or prevent diseases, pain, infection, or discomfort in humans or other mammals. Examples include substances that can reduce or eliminate pain or reduce the possibility or severity of infection, e.g., local anesthetic agents, anti-infection agents including anti-bacterial, anti-viral, anti-fungal, anti-biofilm formation agents, etc.

"Local anesthetic agent(s)" includes both amide type local anesthetic agents such as lidocaine, prilocaine, articaine, bupivacaine, dibucaine, etidocaine, levobupivacaine, mepivacaine, piperocaine, ropivacaine, trimecaine, as well as ester type local anesthetic agents such as such as benzocaine, chloroprocaine, cocaine, cyclomethycaine, dimethocaine, propoxycaine, procaine, proparacaine, and tetracaine. In one embodiment, the local anesthetic agent used can be in its base form.

"Rubber" when used to describe the wall material of a medical catheter or tube means any elastic or soft material typically used to make the wall or part of the wall of a medical catheter or tube, and includes, without limitation, silicone, latex, polyurethane, copolymers having urethane monomer units, and the combination thereof. "Rubber" can be used interchangeably with "polymer" in the present disclosure.

"Anti-infection agent(s)" includes all substances that are capable of preventing viral, fungal, or bacteria infections or reducing the severity of such infections, such as, without limitation, antibiotics, metallic anti-infectives such as a silver compound, and the like. "Anti-infection agent(s)" also includes substances that prevent or inhibit the formation of biofilm on the surfaces of medical catheters, tubes, and devices. Thus, anti-infection agents include, without limitation, chlorhexidine, silver sulfadiazine, silivier chloride, silver oxide, colloidal silver, triclosan, nitrofurazone, minocycline, rifampicin, ciprofloxacin, fosfomycin, vancomycin, tobramycin, cefamandol, cephalothin, carbenicillin, amoxicillin, gentamicin, flucloxaxillin, ceragenins, flucanazole, furanone, echinocandins, amphotericins, gendine, chitosan, IgG, cephalosporin, ethylenediamine tetraacetic acid (EDTA), metal binding chelators, and/or biofilm inhibiting peptides.

"Silver compound" is a substance that contains the element silver, and can include substances that produce silver ions in a solution comprising water. Silver compounds include, without limitation, silver nitrate, silver sulfadiazine, silver oxide, and colloidal silver including elemental colloids of silver and alloys thereof.

"Loading solution" is a solution used to load the drug into the wall of a catheter or tube. In a typical use, the drug can be placed (but not necessarily completely dissolved) in a loading solution. The catheter or the tube (or at least the part of its surface intended for drug release) can be immersed into the loading solution for a period of time so that the drug in the loading solution can be absorbed by the wall of the catheter or tube. In one embodiment, as the drug becomes absorbed by the wall of the catheter or tube, additional undissolved drug in the loading solution can become dissolved in the loading solution, thereby providing additional dissolved drug for further absorption in the wall of the catheter or tube.

Additionally, when referring the "loading solution" used to load a drug into a medical catheter or tube (or other medical device), it is understood that the loading parameters can have quite a wide range. In one specific aspect, a useful range can be from 0.2 mL to 10 mL for each $cm^2$ of the wall surface area of a catheter or tube (or other medical device) to be loaded with the drug. For example, if a Foley catheter has an outer wall surface area of 56 $cm^2$, the volume of the loading solution can be from 11.2 mL to 560 mL. In some aspects, it can be advantageous to use a relatively small volume of loading solution, because when the drug loading process is essentially complete, a smaller volume of loading solution can mean higher percentage of the drug has been loaded into the catheter or tube. This may mean lower total amount of the drug in the system (in the catheter and in the solution), which may mean lower drug exposure risk. Therefore, in some of the embodiments, the volume of the loading solution can be below 0.3 mL for each $cm^2$ of the wall surface area of a catheter or tube to be loaded with the drug.

"Therapeutically effective," is defined as an effect on a mammalian (typically human) subject that is statistically significant ($p<0.05$) when tested in 12 or more subjects.

The phrases "relief of pain," and "clinically relevant reduction of pain" or reduction in "discomfort" or "sensitivity" have the same meaning and can be used interchangeably, and can be defined as an average reduction of 3 points or more from the baseline on an 11-point (0-10) numeric pain rating scale compared with placebo when tested using at least 12 subjects.

The unit "mcg/hour/$cm^2$" means microgram per hour per square centimeter.

"Extended period of time" is defined as a period of at least 24 hours.

The phrase "capable of releasing a drug for an extended period of time" (or similar phrases) means capable of releasing the drug at therapeutically effective rates for an extended period of time. For a local anesthetic agent, this is defined as being capable of releasing the local anesthetic agent at rates sufficient to numb targeted mammalian tissue for that period of time. For lidocaine, this means rates greater than 1 mcg/hour/$cm^2$, typically greater than 5 mcg/hour/$cm^2$, greater than 10 mcg/hour/$cm^2$, and often greater than 15 mcg/hour/$cm^2$. For tetracaine, this means rates greater than 2.5 mcg/hour/$cm^2$, typically greater than 5 mcg/hour/$cm^2$, and more typically greater than 10 mcg/hour/$cm^2$. Other local anesthetics can be used providing similar tissue numbing as would be apparent to one skilled in the art after considering the present disclosure. For anti-infection substances, this phrase means releasing of an anti-viral, antibacterial, anti-fungal, or anti-biofilm formation agent at an effective rate for at least 2 days, at least 3 days, and often at least 5 days or at least 7 days.

The word "solution" is defined as a liquid (solvent) containing partially or completely dissolved solid (solute).

The terms "absorb" or "load" means loading a drug into the wall material of a catheter or tube by letting the drug diffuse into the wall material (as opposed to coating a layer of material containing the drug onto the surface of the catheter or tube).

"Wall" describes the body of the catheter or tube that can be exposed to the loading solution when the catheter is submerged in the loading solution. "Outer wall surface" refers to the surface that typically contacts the body when the tube or catheter is inserted and "inner wall surface" refers to the functional surface where fluid is typically passed in or out.

"Wall concentration" means quantity of a substance (e.g. a drug) absorbed into each unit surface area of the wall of the catheter or tube (The wall surface area is measured from the outer wall surface). For example, if 5 mg of lidocaine is absorbed through a one square centimeter area of the outer wall surface of a Foley catheter, that area of the wall has a wall concentration of lidocaine of 5 mg/$cm^2$, regardless how deep the lidocaine is distributed within the wall material. For example, if a Foley catheter has a outer diameter of 0.6 cm and 236 mg of lidocaine has been absorbed into the wall through a 25 cm length section of the catheter's outer wall surface, the average wall concentration of lidocaine in the 25 cm length section of the wall is 236 mg/(0.6 cm×t×25 cm)=5 mg/$cm^2$. The wall concentration of a drug, as used in the present disclosure, includes only the drug actually absorbed into the wall material and does not include the drug merely sits on the surface of the wall (e.g., that can be removed by a simple wipe).

The terms "immerse" or "submerge" when used to describe keeping the wall of a catheter or tube in the loading solution, includes not only the immersion of the catheter or tube in the loading solution, but also, maintaining part, most, or all of the outer wall of the catheter or tube in the loading solution for a sufficient period of time to allow for drug loading into the walls of the catheter or tube.

The term, "dynamic equilibrium" when used to describe the distribution of a drug in the solution and in the catheter wall includes the situation in which both the drug distribution within the catheter wall material and the distribution between the loading solution and the wall material have reached equilibrium (so that there is no net inflow or outflow of the drug into the wall). It can also include the situation in which the dynamic equilibrium between the solution and wall surface is almost reached except there is still a slight inflow of the drug into the wall due to the diffusing of the drug already in the wall material deeper into the wall material. Thus "dynamic equilibrium" can refer to a situation where the drug in solution and the wall are in "complete" equilibrium, or where there is "substantially complete" equilibrium with only minimal or slight diffusion into the wall. In "substantially complete" equilibrium, the slight drug inflow is defined as a drug inflow into the wall of the catheter or tube whose rate is less than 10% of the peak inflow rate after the catheter is first submerged in the loading solution. In both cases, the tube with drug loaded in the wall thereof will be effective for use in accordance with embodiments of the present disclosure.

When referring to "mucosa," "mucosal tissue," or "mucosal surface," this includes mammalian mucosal and sub-mucosal tissue. Exemplary mucosa sites include urinary tract mucosa, airway mucosa, oral and nasal cavity mucosa, anal mucosa, vaginal mucosa, peritoneal surfaces, etc.

When referring to a "wound" or "wound surface," what is referred to is body surface that is not protected by skin or mucosa, including surgical wounds, trauma wounds, wounds caused by infection or disease (e.g., bed sores), etc.

The term "patient" refers to humans and other mammals.

As used herein, a plurality of drugs, and/or substances may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range.

It is noted that all percentages are in weight, unless specified otherwise.

With this background in mind, a medical catheter or tube capable of releasing drug for at least 24 hours when used in a patient can comprise wall material having an outer wall surface and an inner wall surface, and having a wall area with a wall concentration of drug of at least 1 mg/cm$^2$. The drug can be diffused into the wall material via a loading solution. For example, the drug can include a local anesthetic and/or an anti-infection agent.

In another embodiment, a system of a loading solution and a medical catheter or tube capable of releasing drug for at least 24 hours when used in a patient can comprise a medical catheter or tube and a loading solution. The medical catheter or tube can comprise wall material having an outer wall surface and an inner wall surface. The loading solution can include a drug in which at least a portion of the wall material is submersed. A first portion of the drug can be in the loading solution and a second portion of the drug can be absorbed into at least a portion of the wall material. In one specific example, the wall concentration can be at least 1 mg/cm$^2$. In another specific example, the wall material of the medical catheter or tube and in the loading solution can be in dynamic equilibrium.

In another embodiment, a system of a loading solution and a medical catheter or tube capable of releasing a local anesthetic agent for at least 24 hours when used in a patient can comprise a medical catheter or tube and a loading solution. The medical catheter or tube can comprise wall material having an outer wall surface and an inner wall surface. The loading solution can be used to submerse the medical catheter or tube for at least 30 days, and can include lidocaine, prilocaine, articaine, bupivacaine, dibucaine, etidocaine, levobupivacaine, mepivacaine, piperocaine, ropivacaine, trimecaine, benzocaine, chloroprocaine, cocaine, cyclomethycaine, dimethocaine, propoxycaine, procaine, proparacaine, or tetracaine. In the system, a first portion of the local anesthetic agent remains in the loading solution and a second portion of the local anesthetic agent can be absorbed into the wall material. At least a part of the wall material can have a wall concentration of the local anesthetic agent of at least 1 mg/cm$^2$, and the volume of the loading solution can be in the range of 0.2 to 10 mL for each cm$^2$ of the outer wall surface area of the catheter or tube exposed to the loading solution.

In another embodiment, a method of making a medical catheter or tube capable of releasing a drug for at least 24 hours can comprise the steps of placing at least a portion of a medical catheter or tube into a loading solution so that a wall of the medical catheter or tube contacts the loading solution, the loading solution comprising a drug and more than 50% water by weight; and diffusing the drug of the loading solution into the wall until dynamic equilibrium is reached.

In another embodiment, a method of making a medical catheter or tube capable of releasing a local anesthetic agent for at least 24 hours can comprise placing at least a portion of a medical catheter or tube into a loading solution so that an outer wall surface contacts the loading solution, the loading solution having a pH greater than about 7.0 and including a local anesthetic agent and more than 50% water by weight. An additional step includes waiting at least 15 days with the outer wall surface in contact with the loading solution before using the medical catheter or tube for a medical purpose.

In another embodiment, a urinary catheter assembly for immersing in a loading solution without allowing the loading solution to enter the inside of the urinary catheter can comprise a urinary catheter and a sealing mechanism. The urinary catheter can include a patient end, a discharge end, a balloon closer to the patient end, a patient end opening on the catheter between the balloon and the patient end, and a discharge end opening on the discharge end. The urinary catheter can be configured so that the patient end and the patient end opening is insertable into the discharge end opening on the discharge end to form an insertion region. The sealing mechanism can be configured to seal the insertion region between the two ends such that when the catheter is submerged into a loading solution, no solution can get to the inside of the urinary catheter.

In another embodiment, a urinary catheter system can comprise a urinary catheter and a loading solution. The urinary catheter can comprise wall material having an outer wall surface and an inner wall surface. The loading solution, which can include lidocaine, can be used so that at least a portion of the outer wall surface has been submersed for at least 30 days. The pH of the loading solution can be greater than about 7.0, the viscosity of the loading solution can be greater than about 300 centipoise, and at least one portion of the urinary catheter can have a wall concentration of lidocaine of at least 1 mg/cm$^2$. The volume of the loading solution can also be in the range of 0.2 to 10 mL for each cm$^2$ of the outer wall surface area submersed in the loading solution.

In another embodiment, a urinary catheter system can comprise a urinary catheter having wall material with an outer wall surface and an inner wall surface, a loading solution in which at least a portion of the outer wall surface is submersed, and a local anesthetic in the loading solution and absorbed into the wall material. The pH of the loading solution can be greater than about 7.0, the viscosity of the loading solution can be greater than about 300 centipoise, and at least one portion of the urinary catheter can have a wall concentration of local anesthetic of at least 5 mg/cm$^2$.

In another embodiment, a urinary catheter is disclose that has an inner wall surface and an outer wall surface, the outer wall surface having a wall area with a tetracaine wall concentration of at least 1 mg/cm$^2$, and in some embodiments, at least 5 mg/cm$^2$.

In another embodiment, a urinary catheter is disclose that has an inner wall surface and an outer wall surface, the outer wall surface having a wall area with a lidocaine wall concentration of at least 1 mg/cm$^2$, and in some embodiments, at least 5 mg/cm$^2$.

In still another embodiment, a drainage tube capable of releasing a local anesthetic agent for at least 24 hours when used in a patient is disclosed where the drainage tube has an inner wall surface and an outer wall surface, the outer wall surface having a wall area with a local anesthetic agent wall concentration of at least 5 mg/cm$^2$.

In another embodiment, a drainage tube system can comprise a drainage tube comprising wall material having an outer wall surface and an inner wall surface. Also included is a loading solution in which at least a portion of the outer wall surface is submersed. A local anesthetic is present in the loading solution and absorbed into the wall material. At least a portion of the wall material has a wall concentration of the local anesthetic agent of at least 1 mg/cm$^2$.

In another embodiment, a drainage tube system can comprise a drainage tube with wall material having an outer wall surface and an inner wall surface, and a loading solution in which at least a portion of the outer wall surface has been submersed for at least 30 days. At least one of lidocaine or tetracaine can be present in the loading solution and absorbed into the wall material. The pH of the solution can be greater than about 7.0, and at least one part of the wall material of the drainage tube can have a wall concentration of lidocaine or tetracaine of at least 1 mg/cm$^2$.

In another embodiment, a medical drainage tube is disclosed having an inner wall surface and an outer wall surface, the outer wall surface having a wall area with a tetracaine wall concentration of at least 1 mg/cm$^2$, or even at least 5 mg/cm$^2$.

In another embodiment, a medical drainage tube is disclosed having an inner wall surface and an outer wall surface, the outer wall surface having a wall area with a lidocaine wall concentration of at least 1 mg/cm$^2$, or even at least 5 mg/cm$^2$.

In another embodiment, a medical catheter or tube system can comprise a medical catheter or tube and a container with a fluid retention ring. When the medical catheter or tube is positioned in the fluid retention ring, the container is sealed. The system can also include a loading solution for loading drug into the medical catheter or tube within the container.

In another embodiment, a method for loading a drug into the a surface wall of a medical device can comprise keeping a surface of a medical device in a loading solution comprising a drug for at least 15 days, wherein more than 50% of the drug molecules exist in unionized form in the loading solution.

In another embodiment, a medical catheter or tube system can comprise a medical catheter or tube comprising wall material having an outer wall surface and an inner wall surface, and a loading solution comprising a silver compound in which at least a portion of the outer wall surface has been submersed for at least 30 days.

In another embodiment, a medical device capable of releasing a drug for at least 24 hours when used in a patient can comprise an outer wall surface having a wall area with a wall concentration of a drug of at least 1 mg/cm$^2$, wherein the drug is diffused into material of the wall via a loading solution.

Figure 2:
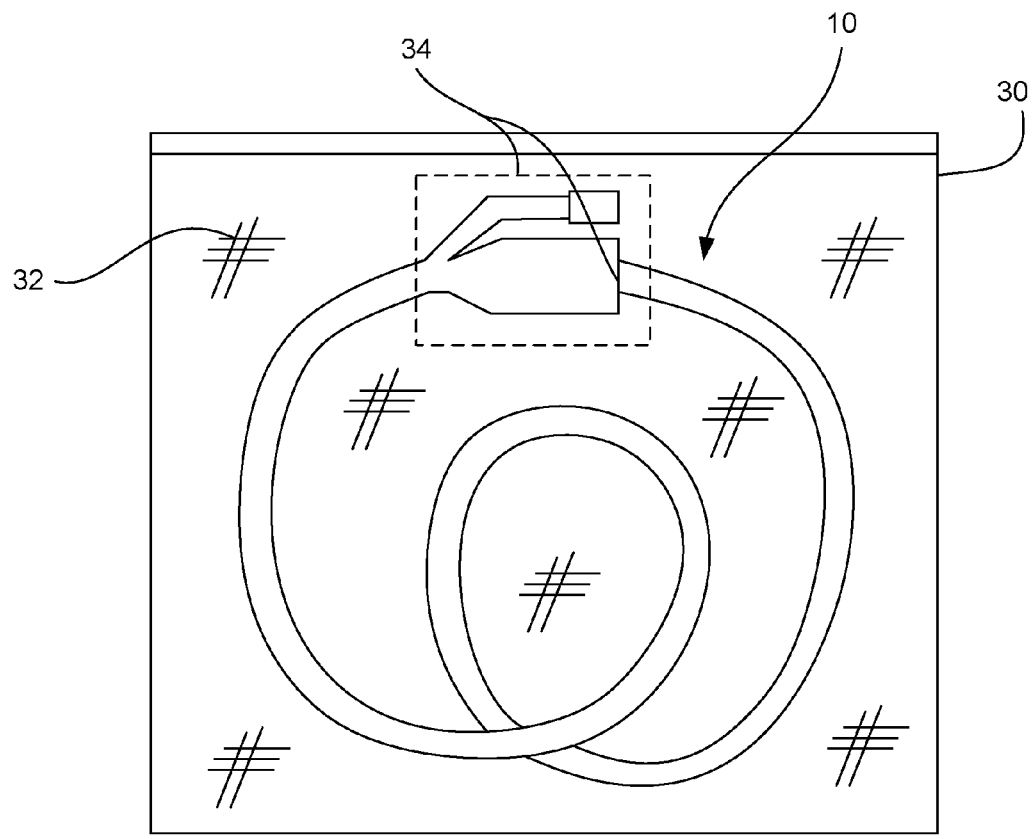
FIG. 2 is a schematic drawing of an embodiment of the present disclosure which includes a catheter, a closed container, a loading solution, and a sealing mechanism.
Figure 3:
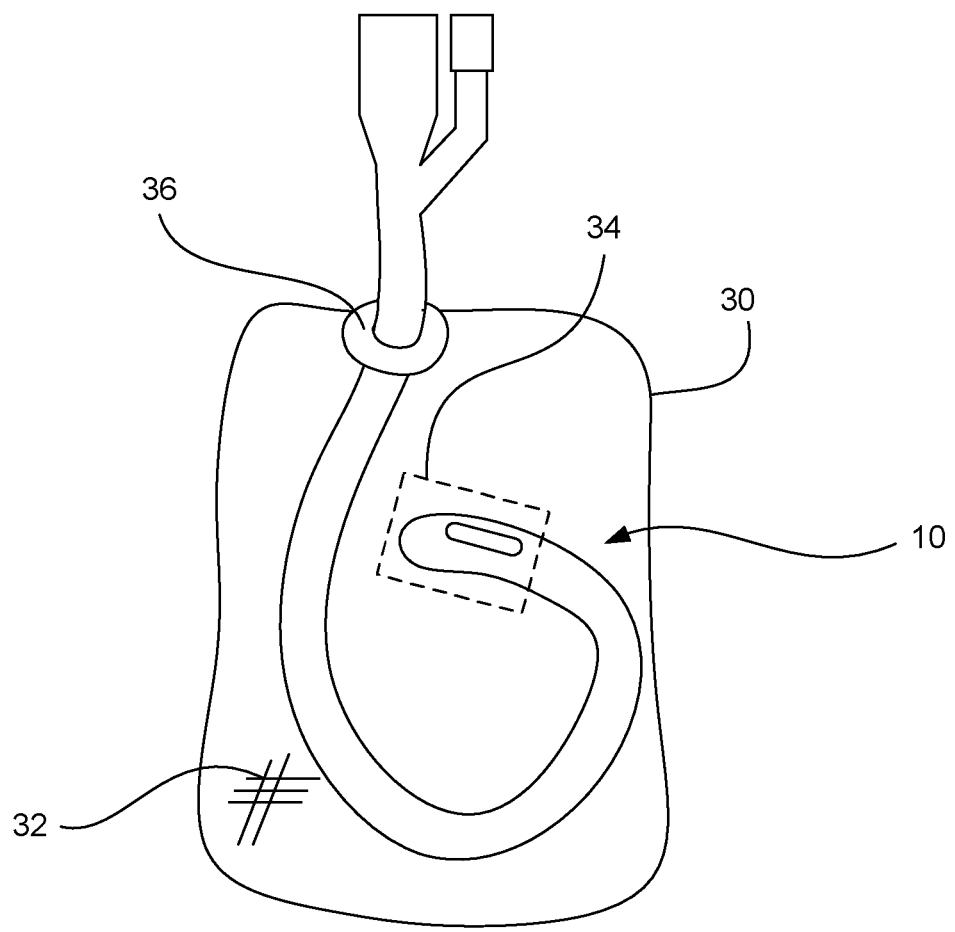
FIG. 3 is a schematic drawing of another embodiment of the present disclosure which includes a catheter, a container, a loading solution, and a fluid retention ring assists in closing the container when the catheter is in place.

In each of the following embodiments, which are related to the embodiments described above and elsewhere herein, reference is made to a medical catheter or tube, or a medical device. For exemplary purposes, a urinary (Foley) catheter is shown by way of illustration in FIG. 1, and a systems in accordance with embodiments of the present disclosure are shown in FIGS. 2 and 3. However, other medical catheters and tubes can likewise be similarly prepared, and it is noted that the Foley catheter is shown merely to illustrate one possibility in accordance with examples of the present disclosure.

Specifically in FIG. 1, a urinary catheter 10 is shown which includes a patient end 12, and a discharge end 14. Close to the patient end is a patient end opening 16 and a balloon 18. The balloon is inflated with air or filled with a liquid through a channel 20 once the patient end is inserted into the bladder of the patient, which keeps the device from being inadvertently removed. When in place, urine can drain from the bladder through the patient end opening 16, the urinary channel 22, and the discharge end opening. The urinary catheter has a wall 24, an outer wall surface 26, and inner wall surface 28. Other modifications of this type of catheter can also be used in accordance with embodiments of the present disclosure. For example, there are catheter systems with three channels instead of two, there are variously configured balloons, and variously configured openings and channels, etc. The mechanical configuration of the specific catheter is not necessarily part of the invention in every embodiment, as the drugs of the present disclosure can be used in many differently configured medical catheters and tubes, and even devices. Thus, it is noted that many different types of tubes can be used in accordance with embodiments of the present disclosure.

FIG. 2 shows the urinary catheter 10 in a rolled up configuration, and contained within a sealed container 30. Within the sealed container is a loading solution 32 which is described herein at length. Also shown is a schematic of a sealing mechanism 34, particularly its location and purpose is for protecting the urinary channel from being filled with the loading solution (it is noted that in some embodiments the urinary channel can be filled with the loading solution for faster and/or more even loading of the drug into the wall. In those embodiments, the loading solution can be drained from the urinary channel before the catheter is used in the patient). In this particular embodiment, the patient end 12 is inserted into the urinary channel 22 at the discharge end 14, covering the patient end opening (not shown). The sealing mechanism can be used to seal the insertion point between the two ends such that when the catheter is submerged into a solution, little to no solution can get to inside of the catheter. Other systems can also be utilized, with the primary goal of preventing loading solution from substantially entering the urinary channel, thereby becoming clogged prior to use.

Referring now to FIG. 3, a urinary catheter 10 is shown in a rolled up configuration and partially contained within a sealed container 30. Within the sealed container is a loading solution 32. Also shown is a schematic of a sealing mechanism 34 which seals an opening at the end of the catheter. In addition to the sealing mechanism, this embodiment also includes a fluid retention ring 36. Specifcially, the loading solution can be loaded within the container, and the catheter can be positioned through fluid retention ring and partially within the container. In this configuration, the fluid is retained within the sealed container, as the catheter provides a temporary seal in combination with the fluid retention ring. To remove the catheter for use, the user can simply pull the exposed end of the catheter from the sealed container (through the fluid retention ring) and the catheter is ready to use with little to no further preparation.

Turning to more specific embodiments, a system of the present disclosure is prepared in accordance with the following process: a catheter, such as a Foley catheter, (whose entire or part of the wall material is either silicone or latex rubber and whose openings are blocked), is immersed into a water-based solution containing mostly unionized lidocaine. The pH of the solution is greater than 6.5, and typically greater than about 7.0, and most typically greater than about 7.5. For a lidocaine in water solution, for example, solubility and percentage of ionized molecules decreases as the pH increases. As the rubber wall of the catheter absorbs the unionized lidocaine dissolved in the solution, lidocaine in the undissolved (solid) form continues to dissolve into the solution. Thus, as dissolved drug is absorbed into the catheter wall, additional undissolved drug can go into the solution, thereby providing more drug in the solution to cause it to continue being driven into the catheter wall. The temperature of the solution can be increased (e.g., 60° C.) for a period of time (e.g. 12 to 48 hours), to increase the speed of lidocaine absorption into the catheter wall, though this is not required.

After the desired amount of lidocaine is absorbed into the catheter wall, the catheter is retrieved from the solution, dried, and stored. When it comes the time to use it, it is inserted into the urinary tract of the patient in the same way as an ordinary Foley catheter (usually with the help of an ordinary lubricant which has no drug-releasing function). Once the catheter is in the urinary tract, lidocaine in the rubber wall slowly diffuses out of the wall and into the mucosal surface in contact with the catheter wall. The mucosal surface is numbed by the continuous presence of lidocaine until the lidocaine in the catheter wall is depleted to the point that the lidocaine release rate drops to below the therapeutically effective rate.

In another more specific embodiment, a system of the present disclosure is prepared in accordance with the following process: a Foley catheter is immersed into a water-based solution (either viscous or water-like viscosity) containing lidocaine base solid (so the lidocaine base quantity in the solution is more than what the solution can dissolve). The pH of this solution with lidocaine is typically greater than about 7.0, or even greater than 7.5, such that most of the lidocaine in the solution exists in the unionized form. The solution, with the catheter in it, is then sealed into a closed container which is then placed into storage (e.g., a warehouse). The rubber wall of the catheter starts to absorb the lidocaine dissolved in the solution. As the dissolved lidocaine gets absorbed into the catheter wall, lidocaine in the undissolved form in the solution continues to dissolve into the solution. After sufficient time (typically days or weeks), the wall of the Foley catheter has absorbed enough lidocaine for the purpose of extended release of lidocaine. However, the catheter continues to stay in the solution (which is in the sealed container) for the entire or most of the duration of storage prior to use. Sometime during storage (typically many days to weeks at room temperature), the lidocaine in the solution and that in the wall of the catheter reach dynamic equilibrium (meaning the rate of lidocaine diffusing from the solution into the catheter wall equals the rate of lidocaine diffusing out of the catheter wall into the solution). As a result, there is no net lidocaine permeation into or out the catheter wall after the dynamic equilibrium is reached. Of course, this dynamic equilibrium between of the solution and catheter wall can be altered as the lidocaine already absorbed into the catheter wall diffuses deeper into the wall material. Eventually, the lidocaine distribution inside the wall material will also reach equilibrium. At that point, the distribution of lidocaine in the wall material and in the solution will not change anymore. The quantity of lidocaine solid initially in the solution can be such that when the dynamic equilibrium is reached, there is no more solid lidocaine in the solution. Optionally, the quantity of lidocaine solid initially in the solution can be such that when the dynamic equilibrium is reached, there is no more solid lidocaine in the solution and the concentration of dissolved lidocaine in the solution is at or very close to the saturation point (as measured at 25° C.). When the concentration of unionized lidocaine dissolved in the solution is close to the saturation point of the unionized lidocaine (i.e. greater than 90% of the saturation concentration), the dynamic equilibrium is reached, the amount of lidocaine loaded into the catheter wall is close to the maximum amount that this method can load, and thus the catheter can provide maximum or near maximum duration of drug release when the catheter is used in a patient.

Optionally, the loading solution can also have the appropriate viscosity and other properties so that it can be used as lubricant for facilitating the insertion of the catheter into the patient's urinary tract. For example, the viscosity of the solution can be in the range of 300 to 600,000 centipoise, and often in the range of 3,000 to 150,000 centipoise. When it comes the time to use such a system, the openings are unblocked (if they were blocked) and there may be no need to smear additional lubricant onto the catheter before it is inserted into the patient's urinary tract because the viscous solution that is already on the surface of the catheter wall when it is retrieved from the loading solution can perform the function of the lubricant. Once the catheter is in the urinary tract, lidocaine in the wall slowly diffuses out of the wall and into the mucosal surface in contact or in close proximity with the catheter wall. The mucosal surface is numbed by the continuous presence of lidocaine until the lidocaine in the wall is depleted to the point that therapeutically effective release rates cannot be maintained. The catheter in this embodiment can reduce the sensitivity of a part of or entire urinary tract for at least 24 hours, and often, at least 72 hours. This method of loading the drug into the catheter wall as described above can be referred to as a dynamic equilibrium loading method (or technology).

The time it takes to reach the dynamic equilibrium depends on several factors, including the initial drug concentration in the loading solution, the loading solution temperature, the catheter wall material, etc. However, it is typically days or weeks. One advantage of the dynamic equilibrium loading method is that the process of reaching dynamic equilibrium can take place automatically without any work done by the manufacturing personnel, in one embodiment. For most, if not all medical device and pharmaceutical products, the time between when the product is made and when it is actually used is at least 30 days, and most likely much longer. When referring to "when the product is made," what is meant is that the active manufacturing operation on the product is completed. Product release test work is not included in the definition of active manufacturing operation on the product. Allowing the drug to become absorbed into the wall represents passive manufacturing largely after active manufacturing is completed. Therefore, the catheter can be submerged in the loading solution for at least 30 days, and even for at least 90 days, before it is used. That would be adequate time for the system to reach, or at least be very close to, the dynamic equilibrium. To shorten the time to reach dynamic equilibrium, the system can be placed in a higher temperature environment for a certain period of time (e.g., 40° C. for 15 days). In a more general embodiment, the higher temperature range can be from 35° C. to 70° C., and the time frame can independently be from 12 hours to 30 days.

Similar to the preparation of the Foley catheter above, in one specific embodiment, a drainage system can be prepared in accordance with the following process: a drainage tube is immersed into a water-based solution with such a pH that most of the lidocaine in it is in the unionized form. The tube and the solution are then sealed into a closed container. The container has an opening to accommodate a sealing ring whose size and shape matches that of the cross-section of the tube. One end of the drainage tube is outside the container through the sealing ring (referred as fluid retention ring in FIG. 3 above), so the part of the tube outside of the container through the fluid retention ring is not exposed to the solution. It is noted that "fluid retention ring," as used in the present disclosure, does not necessarily mean a round-shaped object. It can be some other shapes but has to be able to accommodate the cross-section of the tube without a gap. The system of the catheter in the loading solution (in a sealed container) is placed into storage (e.g., a warehouse). As the rubber wall of the tube absorbs the lidocaine dissolved in the solution, lidocaine in the solid form in the solution continues to dissolve into the solution. After sufficient time (typically days or weeks), the wall of the drainage tube has absorbed enough lidocaine for the purpose of extended release of lidocaine. However, in one embodiment, the tube continues to stay in the solution. Eventually, the lidocaine in the solution and that in the wall of the tube reach dynamic equilibrium. The quantity of lidocaine solid initially in the solution can be such that when the dynamic equilibrium is reached, there is no more solid lidocaine in the solution. Optionally, the quantity of lidocaine solid initially in the solution is such that when the dynamic equilibrium is reached, there is no more solid lidocaine in the solution and the concentration of dissolved unionized lidocaine in the solution is at or very close to the saturation point, e.g., is greater than 90% of the solubility of unionized lidocaine in the solution (as measured at 20° C.). When it comes the time to use the drainage tube, the tube is pulled out of the container through the fluid retention ring which "wipes" the solution from the surface of the tube so that the tube pulled out of the container is dry or has only small amount of the solution (less than 1 mm layer) on its wall and can be used as an ordinary "dry" tube. The openings of the tube are unblocked prior to use. Once the drainage tube is in use in the patient, its wall is in contact with the wound surface. Lidocaine in the rubber wall slowly diffuses out of the wall and onto the wound surface. The wound surface is numbed by the continuous presence of lidocaine for an extended period of time. The use of systemic pain control drug may be reduced.

In another embodiment, a system is made in accordance with the following process: a Foley catheter with openings blocked off is placed into a water-based loading solution containing tetracaine (base) solid (so the tetracaine base quantity in the solution is more than what the solution can dissolve). The pH of this solution with tetracaine solid is greater than about 7.0. As the rubber wall of the catheter absorbs the tetracaine dissolved in the solution, tetracaine in the solid form continues to dissolve into the solution. Optionally, the temperature of the solution can be increased [e.g., 45° C., (tetracaine's melting point is about 41° C.) to increase the speed of tetracaine absorption into the catheter wall. After the desired amount of tetracaine is absorbed into the catheter wall, the catheter is retrieved from the solution, dried, and stored. When it comes the time to use it, it is inserted into the urinary tract of the patient in the same way as an ordinary Foley catheter (usually with the help of ordinary lubricant which has no drug-releasing function). Once the catheter is in the urinary tract, tetracaine in the rubber wall slowly diffuses out of the wall and into the mucosal surface in contact with the catheter wall. The mucosal surface is numbed by the continuous presence of tetracaine until the tetracaine in the wall is depleted to the point that therapeutic tetracaine release rates cannot be maintained. There is noticeable difference between the system in this embodiment and that in the embodiments in which lidocaine is used as the local anesthetic agent. Tetracaine is more hydrophobic (more lipophilic) than lidocaine, and thus has better affinity with the rubber catheter wall. This means: (1) once loaded into the rubber wall, tetracaine has lower tendency to diffuse out of the wall and present itself as a powder on the surface of the wall, and (2) due to its better affinity with the catheter wall material, tetracaine is released out of the wall at slower rates than lidocaine when in the patient's urinary tract. However, tetracaine also has better binding with mucosal tissues (longer duration of numbing effect) than lidocaine, so even the lower release rates of tetracaine are still sufficient to numb the mucosa for extended period of time.

Although the systems in the embodiments in which the catheter or tube is retrieved from the loading solution after the desired amount of the drug has been absorbed into the wall and dried before being put into storage can work well as described, lidocaine in the rubber wall may diffuse out of the rubber material and present itself as a powder (lidocaine crystals) on the surface of the wall during storage. This is not harmful, but it can significantly reduce and vary the amount of the drug actually stored in the wall, resulting in shortened and variable drug release durations. Therefore, comparing the systems of the present disclosure in the various embodiments, the embodiments that utilize a loading solution in which the catheter or tube is submerged during the entire or most of the storage period, and optionally, employing a loading solution that can also work as a lubricant, have the following advantages: (1) It is easier to manufacture as its absorption process (the process of loading the drug into the catheter wall) mostly takes place automatically instead of utilizing active manufacturing operation. (2) The loaded catheter does not need to be dried during the manufacturing process. (3) The catheter can hold more and more stable amount of the drug in the catheter wall, an advantage provided by the dynamic equilibrium feature of the system. (4) The catheter system is easier to use since the loading solution can also serve as the lubricant so that the physician can save the step of applying lubricant before inserting the catheter into the patient's urinary tract.

In many of the embodiments of the present disclosure, a Foley catheter is submerged in a solution for extended periods of time (e.g. during the entire storage or shelf time). It can be useful to seal off the openings on the catheter so that no solution can get into the inside of the catheter (although this is optional and not required). There are many ways to seal off the openings, such as using tapes that are not penetrable by the solution to cover the openings, using stoppers to block the openings, etc. One method (assembly) that can be used is as follows: the part of the catheter with the openings between the balloon and the patient end is inserted into the opening on the discharge end. A sealing mechanism is used to seal the insertion point between the two ends such that when the catheter is submerged into a solution, no solution can get to inside of the catheter. The sealing mechanism can be a ring-shaped plastic stopper with an outer diameter suitable for blocking the opening on the discharge end, and an inner diameter such that when the stopper is placed between the balloon and the patient end (with the catheter though the middle of the ring), and there is no gap between the stopper and the catheter. When the patient end with such a stopper placed between the balloon and the patient end is inserted into the opening of the discharge end, the inside of the catheter is isolated from the external environment. The sealing mechanism needs to be removed before the catheter is inserted into the patient's urinary tract. FIG. 2 discussed above schematically depicts aspects of these sealing mechanism embodiments.

In another embodiment of the present disclosure, the system is similar to that of one of the aforementioned embodiments, except that there is a silver compound, as the only drug or in addition to the aforementioned local anesthetic agent, is in the solution. The silver compound may or may not be completed dissolved initially. In another embodiment of the present disclosure, the system is similar to that of one of the aforementioned embodiments, except that there is a compound in the solution that is selected from the group of chlorhexidine, silver sulfadiazine, silver chloride, silver oxide, colloidal silver triclosan, nitrofurazone, minocycline, rifampicin, ciprofloxacin, fosfomycin, vancomycin, tobramycin, cefamandol, cephalothin, carbenicillin, amoxicillin, gentamicin, flucloxaxillin, ceragenins, flucanazole, furanone, echinocandins, amphotericins, gendine, chitosan, IgG, cephalosporin, ethylenediamine tetraacetic acid (EDTA), metal binding chelators, biofilm inhibiting peptides, and combinations thereof.

In another embodiment, the system is similar to that of one of the aforementioned embodiments, except that after the container containing the catheter and the solution is sealed, and the system is exposed to an autoclaving temperature. This can sterilize the solution and the catheter, as well as accelerate the drug loading process. Alternatively, the sealed system can be exposed to a radiation source for sterilization.

In another embodiment, the system is similar to that in the aforementioned embodiments with a lidocaine or other local anesthetic wall concentrations of at least 1 mg/cm$^2$ within the catheter wall. Optionally, the lidocaine wall concentration can be at least 5 mg/cm$^2$, at least 10 mg/cm$^2$, or even at least 15 mg/cm$^2$.

In still another embodiment of the present disclosure, the system is similar to that in the aforementioned embodiments, and the catheter (after the dynamic equilibrium is reached) is capable of releasing lidocaine at rates greater than 1 mcg/hour/cm$^2$ continuously for at least 24 hrs when submerged in a 0.9% sodium chloride-in-water solution. The 0.9% sodium chloride in water solution is used to characterize the drug release rate and duration. Although the real target of the released drug is the mucosa of the urinary tract or wound surface or other tissues, the release rate is controlled by the diffusion speed of the drug out of the catheter or tube wall material. Therefore, for characterizing the release rate and duration, the 0.9% sodium chloride in water solution is a reasonably close and simple surrogate for mammalian tissue, such as human tissue. Unless specified otherwise, the volume of the 0.9% sodium chloride in water solution used to characterize the drug release rate and/or duration is 10 mL for each square centimeter of the catheter or tube wall surface to be tested, and the solution temperature is from 35° C. and 37° C. For example, to test the lidocaine release rate of a Foley catheter whose outer surface area is 56 cm$^2$, 560 mL of the 0.9% sodium chloride in water solution is used. Solutions of difference compositions and volume may also be used for this test, and the above composition and volume are only meant to standardize a test.

In still another embodiment, the system is similar to that in the aforementioned embodiments, and at least a part of the catheter wall (after the dynamic equilibrium is reached) is capable of releasing lidocaine or other local anesthetics continuously at rates greater than 5 mcg/hour/cm$^2$, greater than 10 mcg/hour/cm$^2$, or even greater than 15 mcg/hour/cm$^2$, for at least 24 hrs when submerged in a 0.9% sodium chloride-in-water solution.

In another embodiment, at least a part of the catheter wall (after the dynamic equilibrium is reached) is capable of releasing lidocaine or other local anesthetics continuously at rates greater than 5 mcg/hour/cm$^2$, greater than 10 mcg/hour/cm$^2$, or even greater than 15 mcg/hour/cm$^2$, for at least 72 hrs when submerged in a 0.9% sodium chloride-in-water solution.

In another embodiment, at least a part of the catheter wall (after the dynamic equilibrium is reached) is capable of releasing lidocaine or other local anesthetics continuously at rates greater than 5 mcg/hour/cm$^2$, greater than 10 mcg/hour/cm$^2$, or even greater than 15 mcg/hour/cm$^2$, for at least 24 hours, and often at least 72 hrs, when in contact with urinary tract mucosa, e.g., human urinary tract mucosa.

In another embodiment, the system is similar to that in the aforementioned embodiments which comprises lidocaine as the local anesthetic agent, except that the lidocaine is replaced or admixed with a local anesthetic agent such as prilocaine, articaine, bupivacaine, dibucaine, etidocaine, levobupivacaine, mepivacaine, piperocaine, ropivacaine, trimecaine, benzocaine, chloroprocaine, cocaine, cyclomethycaine, dimethocaine, propoxycaine, procaine, paracaine, tetracaine, and mixtures thereof.

In still another embodiment, a system is similar to that described above, except that the Foley catheter is replaced by a medical drainage tube and/or the lidocaine is replaced by tetracaine or another appropriate local anesthetic, and that the system is to be used for patient's wound instead of urinary tract.

It is notable that most, if not all, commonly used local anesthetic agents are bases. They have high solubility in water based (aqueous) solutions with low pH, and low solubility in solutions with high pH. For example, lidocaine's solubility in water is greater than 20% when the pH of the water is lower than 5, but the solubility drops to below 0.5% when the pH is greater than 8. Also, the fraction of lidocaine in unionized form, which is much less soluble in water than the ionized molecules, increases with increasing pH. In the present disclosure, the loading solutions used to load local anesthetic agents into the catheter or tube wall have a pH such that most of the local anesthetic agent in the solution exist in the unionized form (mostly undissolved). This approach is counter-intuitive since only the local anesthetic agent dissolved in the loading solution can be absorbed by the rubber wall, an ordinary person skilled in the art would naturally try to maximize the concentration of the drug actually dissolved in the loading solution to maximize the loading speed and quantity. For a base drug such as a lidocaine, this approach would mean using a salt form of the local anesthetic agent (i.e. lidocaine HCl) or other methods to make the pH of the solution significantly below the pKa of the drug. Indeed, almost all commercially available lidocaine solutions have pH lower than about 5.5. (lidocaine's pKa is about 7.9). By using a low pH (e.g. 5.5 or lower), one can easily dissolve more than 20% lidocaine in an aqueous solution. However, in accordance with that disclosed herein, the opposite conclusion is reached. Specifically, it has been discovered that using high solution pH (low solubility) is more effective in loading the local anesthetic into the catheter or tube wall. Some reasons may include the following: Silicone and latex rubbers are hydrophobic materials. Ionized drug molecules, such as most of lidocaine molecules in a solution with a pH much lower than lidocaine's pKa, are hydrophilic. A typical commercially available lidocaine jelly or solution has pH of 5.5 or lower, so practically all the lidocaine molecules in the typical jelly or solution are ionized and dissolved. However, hydrophilic substances do not like to permeate into hydrophobic materials. Therefore, even if there is a high concentration of the dissolved drug (i.e. ionized lidocaine) in the solution, the rubber wall will not absorb very much. On the other hand, unionized drug molecules are usually less hydrophilic and thus have better affinity with the rubbers than in the ionized ones, although they usually have much lower (but not zero) water solubility. For example, unionized lidocaine molecules that are dissolved in the loading solution, although less than 0.5%, have much better affinity with silicone or latex rubber than ionized lidocaine molecules do. This factor of better affinity more than offsets the factor of lower concentration, making the high pH loading solutions the better choice than the lower pH loading solutions.

When a catheter or tube's rubber wall is submerged into a loading solution with a pH high enough such that most of the lidocaine molecules are unionized, the rubber wall absorbs the dissolved unionzed lidocaine at high rates, despite that unionized lidocaine's concentration is very low (limited by the low solubility of the unionized species). As the dissolved unionzed lidocaine leaves the solution and enters the rubber wall, undissolved lidocaine continues to dissolve into the solution and maintains the concentration of the dissolved unionzed lidocaine at saturation. If the process is allowed to continue, the lidocaine in the rubber wall and that in the solution will eventually reach dynamic equilibrium. At that point, if the loading solution initially contained sufficient amount of lidocaine (even if most of it is in undissolved form), the rubber wall will contain much more drug than what a lower pH solution can load.

The above illustration also applies to drugs other than lidocaine as well. The factor to consider with other drugs is to use a loading solution pH such that most of the drug in the load solution initially is unionized. Thus, the use of other local anesthetics and drugs is contemplated by the present disclosure.

In the embodiments of the present disclosure, the local anesthetic agent is absorbed or loaded into the wall material of the catheter or tube instead of in an additional layer of material coated on the wall surface for the purpose of attaching the local anesthetic agent to the catheter or tube. This is specific distinction between the embodiments of the present disclosure and other approaches which merely coat a layer of material containing the drug onto the surface of the walls of these types of devices.

The aforementioned embodiments are applications of a more general method of the present disclosure for loading a drug into the surface of a medical device by submerging a surface of a medical device into a solution comprising a drug for a desired period of time, e.g., at least 12 hours or at least 15 days under heat or at least 30 days with or without added heat. Typically, a 30-day manufacturing time for a medical device product would be infeasible for economical and other reasons. However, with the methods of the present disclosure, the product is submerged in the loading solution for the entire storage duration which is typically longer than 30 days. Thus, the drug loading process can be automatically completed during storage. In other words, all the manufacturing steps except the last step (loading drug into the surface by submerging the product surface in the loading solution for 30 days or more) can be completely within a short time (e.g., less than one day), and the last step can be automatically completed during storage without any additional work.

EXAMPLES

The following examples illustrate the embodiments of the disclosure. However, it is to be understood that the following are only exemplary or illustrative of the application of the principles of the present disclosure. Numerous modifications and alternative compositions, methods, and systems may be devised by those skilled in the art without departing from the spirit and scope of the present disclosure. The appended claims are intended to cover such modifications and arrangements. Thus, while the present disclosure has been described above with particularity, the following examples provide further detail in connection with what are presently deemed to be practical embodiments of the disclosure.

Example 1

Materials:
1. Loading solution: 10% lidocaine (base), 90% water.
2. Foley catheter with silicone rubber wall.

Fifty milliliters of the loading solution, in a glass container, is heated to and maintained at 70° C. so that the lidocaine base in the solution is melted (but mostly not dissolved). The Foley catheter's openings are blocked so that when it is placed in the solution, the solution cannot get into the inside of the catheter. The catheter is completely submerged in the solution which is stirred periodically. Lidocaine in the solution permeates into the silicone rubber wall of the catheter. After 48 hours, the catheter has absorbed a quantity of lidocaine and is retrieved from the solution. The solution on the catheter surface is wiped off. The catheter is then placed into a sealed pouch and sterilized by autoclaving or radiation. To use this catheter loaded with the lidocaine, it is taken out of the sealed pouch and a lubricant, commonly used in the procedure, is smeared on the surface. The catheter is then inserted into the patient's urinary tract. Once it is in, the surface of the catheter is in contact with the mucosa of the urinary tract. Lidocaine in the catheter wall then slowly permeates out of the wall and enters the mucosa, resulting in extended release of lidocaine from the wall. The patient's mucosa is numbed for an extended period of time (e.g. 72 hours).

Example 2

A Urinary (Foley) catheter has a wall comprising two layers of elastic materials, with the outer layer material being about 1 mm thick layer of silicone elastomer. The urinary catheter is about 30 cm long and about 0.6 cm in outer diameter. The openings of the catheter in both ends are blocked by plastic stoppers of appropriate shapes and sizes. The catheter is completely immersed into 50 mL of a solution having the following components: 1% lidocaine base, 0.4% Cabopol 981, 0.2% NaOH, and 98.4% water. All percentages are in weight. Initially, most (more than 90%) of the lidocaine in the solution is not dissolved and exists in the form of solid particles. The container containing the solution and the catheter is then tightly closed and placed in room temperature. When observed about 90 days later, all lidocaine solid particles have disappeared, indicating that all the lidocaine initially existing as particles are absorbed into the wall of the catheter (by gradually dissolving into the solution first). At that time, the lidocaine in the solution and the lidocaine in the catheter wall have reached dynamic equilibrium. The solution is clear and free of visible particles, and has appropriate viscosity to be used as lubricant for facilitating the insertion of the catheter into the patient's urinary tract.

The surface area of the catheter's outer wall is about 56 cm$^2$. There are 500 mg of lidocaine in the solution initially. If more than about 90% of that is absorbed into the catheter wall when the dynamic equilibrium is reached, each cm$^2$ of the catheter wall contains about 8 mg of lidocaine when the dynamic equilibrium is reached.

Prior to use of the catheter, it is taken out of the container and the plastic stoppers that blocked the openings are removed. The loading solution that is already on the wall of the catheter when it is retrieved from the solution is used as the lubricant for facilitating the insertion of the catheter into the patient's unrinary tract. Once the catheter is in the patient's urinary tract, the lidocaine in the wall slowly diffuses out of the wall and into the mucosa in contact with the wall. Since the lidocaine diffusion out of the wall is a slow and controlled process, the permeation of lidocaine into the mucosa, and the numbing effect, can continue for an extended period of time (i.e. longer than 24 hours, or even longer than 72 hours).

Example 3

A system similar to that in Example 2 can be prepared, except that loading solution initially has the following components: 1% lidocaine base, 99% a commercially available water-based lubricant jelly commonly used for facilitating the insertion of Foley catheters into the patient's urinary tract. Many commercially available water-based lubricant jelly can be used in this example, including without limitation, the Surgilube brand and KY Jelly brand Jelly, and products with similar components.

Example 4

Systems similar to that in Example 2 or 3 can be prepared, except that the loading solution initially also contains 0.5% silver sulfadiazine as anti-infection agent [and 0.5% less water (Example 2) or 0.5% LESS jelly (Example 3)].

Example 5

A system similar to that in Example 2 can be prepared, except that the loading solution has 3% lidocaine and 96.4% water (plus 0.4% Cabopol 981, 0.2% NaOH), and 16 mL of the loading solution is used.

Example 6

Systems similar to that in Examples 2-5 can be prepared such that when the catheter is submersed in a 0.9% sodium chloride in water solution, at least some area of the catheter's outer wall surface releases lidocaine at rates greater than 5 mcg/hour/cm$^2$ continuously for at least 48 hours.

Example 7

Systems similar to that in Examples 2-5 can be prepared such that when the catheter is submersed in a 0.9% sodium chloride in water solution, at least some area of the catheter's wall releases lidocaine at rates greater than 10 mcg/hour/cm$^2$ for at least 48 hours.

Example 8

Systems similar to that in Examples 2-5 can be prepared such that when the catheter is submersed in a 0.9% sodium chloride in water solution, at least some area of the catheter's wall releases lidocaine at rates greater than 10 mcg/hour/cm$^2$ for at least 72 hours.

Example 9

Systems similar to that in Examples 2-5 can be prepared such that when the catheter is submersed in a 0.9% sodium chloride in water solution, at least some area of the catheter's wall can release lidocaine at rates greater than 10 mcg/hour/cm$^2$ for at least 120 hours.

Example 10

Systems similar to that in Examples 2-5 can be prepared, except instead of lidocaine, the local anesthetic agent is prilocaine (same weight percentage).

Example 11

Systems similar to that in Examples 2-5 can be prepared, except instead of lidocaine, the local anesthetic agent is bupivacaine (same weight percentage).

Example 12

Systems similar to that in Example 2-5 can be prepared, except instead of lidocaine, the local anesthetic agent is a compound (same weight percentage) is selected from the group of articaine, dibucaine, etidocaine, levobupivacaine, mepivacaine, piperocaine, ropivacaine, trimecaine, benzocaine, chloroprocaine, cocaine, cyclomethycaine, dimethocaine, propoxycaine, procaine, proparacaine, tetracaine, and mixtures thereof.

Example 13

Materials:
1. Loading solution: 3% tetracaine base, 97% water.
2. Foley catheter with silicone rubber wall.

Thirty milliliters of the loading solution, in a glass container, is heated to and maintained at 45° C. so that tetracaine base in the solution is melted (but not dissolved). The Foley catheter's openings are blocked so that when it is placed in the solution, the solution cannot get into the inside of the catheter. The catheter is submerged in the loading solution which is stirred periodically. Tetracaine dissolved in the solution permeates into the silicone rubber wall of the catheter. After 24 hours, the catheter has absorbed a desired quantity of tetracaine and is retrieved from the solution. The solution on the catheter surface is wiped off. The catheter is then placed into a sealed pouch and sterilized by autoclaving or radiation. To use the catheter loaded with the tetracaine, it is taken out of the sealed pouch. A lubricant commonly used in the procedure is smeared on the surface. The catheter is then inserted into the patient's urinary tract. Once it is in the urinary tract, the surface of the catheter is in contact with the mucosa of the urinary tract. Tetracaine in the catheter wall then slowly permeates out of the wall and enters the mucosa, resulting in extended release of tetracaine from the wall. The patient's mucosa is numbed for extended period of time (e.g. 72 hours).

Example 14

Materials:
1. Loading solution: 2% tetracaine base, 98% water.
2. Drainage tube with silicone rubber wall.

The drainage tube is immersed into the loading solution. The volume of the solution is determined by: V=S×0.5, where V is the volume of the solution in milliliters and S is the total outer surface area of the outer wall of the drainage tube in square centimeters. In other words, there is 0.5 mL of the solution for each square centimeter of the outer wall surface. For example, if the drainage tube has an outer diameter of 1 cm and length of 80 cm, its' total outer surface area is about 251 cm$^2$. For such a drainage tube, about 126 mL of the loading solution is used. The loading solution with the drainage tube, in a glass container, is heated to and maintained at 45° C., so that tetracaine base in the solution is melted (but not dissolved). The drainage tube's openings are blocked so that when it is placed in the solution, the solution cannot get into the inside of the tube. Tetracaine in the solution permeates into the silicone rubber wall of the tube. After 48 hours, the tube has absorbed a desired quantity of tetracaine and is retrieved from the solution. The solution on the tube is wiped off. The tube is then placed into a sealed pouch and sterilized by autoclaving or radiation. To use the drainage tube loaded with the tetracaine, it is taken out of the sealed pouch and inserted into the surgical opening of the patient. Once the drainage tube's wall is in contact with the wound surface, tetracaine in the tube wall slowly permeates out of the wall and gets on the wound surface, resulting in numbing the wound surface for an extended period of time (e.g. 72 hours).

Example 15

A system similar to that in Example 13 can be prepared, except that the loading solution has 5% tetracaine and 95% water, and the volume of the solution used is determined by V=S×0.4 (0.4 mL loading solution for each cm$^2$ of the outer wall surface area).

Example 16

Systems similar as that described in Examples 2 through 15 can be prepared, except the loading solution also contains 0.5% of a silver compound (or second silver compound in the case of Example 4) as an anti-infective (and a proportionate amount of water or jelly is removed).

Example 17

Materials:
1. Loading solution: 2% lidocaine base, 98% water.
2. Drainage tube with silicone rubber wall.

The drainage tube, with its openings blocked, is immersed into the loading solution. The volume of the solution is determined by: V=S×0.5, where V is the volume of the solution in milliliters and S is the total outer wall surface area of the drainage tube in square centimeters. The loading solution with the drainage tube, in a glass container, is heated to and maintained at 70° C., so that lidocaine base in the solution is melted (but not dissolved). Lidocaine in the solution permeates into the silicone rubber wall of the tube. After 48 hours, the tube has absorbed a desired quantity of Lidocaine and is retrieved from the solution. The solution on the tube is wiped off. The tube is then placed into a sealed pouch and sterilized by autoclaving or radiation. To use the drainage tube loaded with the Lidocaine, it is taken out of the sealed pouch and as an ordinary drainage tube. Once the drainage tube's wall is in contact with the wound surface, Lidocaine in the tube wall slowly permeates out of the wall and gets on the wound surface, resulting in numbing the wound surface for an extended period of time (e.g. 72 hours).

Example 18

A drainage tube with latex rubber wall is about 60 cm long and has about 0.48 cm in outer diameter. The openings of the tube are blocked before it is completely immersed into 50 mL of a loading solution having the following components: 1% lidocaine base, 0.4% Cabopol 981, 0.2% NaOH, and 98.4% water. Initially, most (more than 70%) of the lidocaine in the solution is not dissolved and exists in the form of solid particles. The container with the solution and the tube therein is tightly closed and placed in room temperature. When observed about 30 days later, all lidocaine solid particles have disappeared, indicating that all the lidocaine initially existed as particles is absorbed into the wall of the tube. At that time, the lidocaine in the solution and the lidocaine in the tube wall have reached dynamic equilibrium.

The surface area of the tube's outer wall is about 90 cm$^2$. There are 500 mg of lidocaine in the solution initially. Since more than 70% of that is absorbed into the tube wall when the dynamic equilibrium is reached, each cm$^2$ of the tube wall contains at least about 3.8 mg of lidocaine at this point in time (wall concentration of lidocaine of greater than 3.8 mg/cm$^2$).

Prior to use the tube, it is taken out of the container and the openings are unblocked. Once the tube is in the patient's surgical wound, the lidocaine in the wall slowly diffuses out of the wall and into the wound surface in contact with the wall. Since the lidocaine diffusion out of the wall is a slow and controlled process, the permeation of lidocaine into the wound, and the numbing effect, can continue for an extended period of time (i.e. longer than 24 hours, or even longer than 72 hours).

Example 19

Systems similar to that described in Examples 17 and 18 can be prepared, except that the drainage tube and the loading solution are sealed into to a closed container with a fluid retention ring, and prior to use, the tube is pulled from the container through the fluid retention ring. The fluid retention ring is shown in FIG. 3.

Example 20

Systems similar to that described in Examples 17-19 can be prepared, except the lidocaine is replaced by tetracaine.

Example 21

A central venous catheter impregnated with anti-infection agent chlorhexidine can be prepared as follows. The loading solution is a water based solution containing 2% chlorhexidine free base (the free base can be produced by first dissolving a salt such as chlorhexidine dichloride and then raising the pH) and an amount of sodium hydroxide that maintains solution's pH at about 10. A central venous catheter made of polyurethane polymer is submerged in the loading solution. At this pH, most of the chlorhexidine free base is undissolved and exists as particles in the solution, but the fraction that is dissolved is highly permeable into the wall of the central venous catheter. The catheter is submerged in the loading solution, whose temperature is increased to 80° C. for at least 8 hours. The catheter is then retrieved from the loading solution, dried, and packaged. During the loading process, sufficient quantities of chlorhexidine have been diffused into the wall of the catheter. When the catheter is inserted into the patient's vein, chlorhexidine slowly diffuses out of the wall of the catheter over many days or even weeks, thus significantly reducing the possibility of infection and/or biofilm formation.

Example 22

A central venous catheter impregnated with anti-infection agent chlorhexidine and which is at dynamic equilibrium is prepared as follows. The loading solution is a water based solution containing 2% chlorhexidine free base (the free base can be produced by first dissolving a salt such as chlorhexidine dichloride and then raising the pH), and an amount of sodium hydroxide that maintains solution's pH at about 10. A central venous catheter made of polyurethane polymer is submerged in the loading solution and the temperature is increased to 60° C. for at least 8 hours. The temperature is then returned to room temperature. The catheter remains in the loading solution during storage for typically at least 30 days. At the initial pH of 10, most of the chlorhexidine free base is undissolved and exists as particles in the solution, but the fraction that is dissolved is highly permeable into the wall of the central venous catheter. As more chlorhexidine permeates into the wall, more undissolved chlorhexidine becomes dissolved into the solution to keep the solution saturated. Eventually most or all of the initially undissolved chlorhexidine is absorbed into the wall. Prior to use, the catheter is retrieved from the loading solution and dried before insertion into the patient's vein. Chlorhexidine slowly diffuses out of the wall of the catheter over many days or even weeks, thus significantly reducing the possibility of infection and/or the formation of biofilm.

While the disclosure has been described with reference to certain embodiments, those skilled in the art will appreciate that various modifications, changes, omissions, and substitutions can be made without departing from the spirit of the disclosure. It is therefore intended that the disclosure be limited only by the scope of the appended claims.

What is claimed is:

1. A medical catheter or tube system capable of releasing drug for at least 24 hours when used in a patient, comprising: a medical catheter or tube comprising wall material having an outer wall surface and an inner wall surface, and a loading solution in which at least a portion of the outer wall surface has been submersed for at least 30 days, wherein the loading solution includes a local anesthetic agent selected from the group consisting of lidocaine, prilocaine, articaine, bupivacaine, dibucaine, etidocaine, levobupivacaine, mepivacaine, piperocaine, ropivacaine, trimecaine, benzocaine, chloroprocaine, cocaine, cyclomethycaine, dimethocaine, propoxycaine, procaine, proparacaine, tetracaine, and mixtures thereof, wherein a first portion of the local anesthetic agent remains in the solution and a second portion of the local anesthetic agent is absorbed into the wall material, wherein at least a part of the wall material has a wall concentration of the local anesthetic agent of at least 1 mg/cm$^2$, and wherein a volume of the loading solution is in the range of 0.2 to 10 mL for each cm$^2$ of the outer wall surface area of the catheter or tube exposed to the loading solution.

2. A method of making the medical catheter or tube comprising: placing at least a portion of the medical catheter or tube of claim 1 into a loading solution so that the outer wall surface of the medical catheter or tube contacts the loading solution, the loading solution comprising a drug and more than 50% water by weight; and diffusing the drug of the loading solution into the wall material until dynamic equilibrium is reached.

3. The method of claim 2, wherein the loading solution has a pH of at least about 7.

4. The method of claim 3, wherein the local anesthetic comprises lidocaine.

5. The method of claim 2, wherein the loading solution further comprises an anti-infective agent, and the anti-infective agent is also absorbed into the wall material.

6. The method of claim 5, wherein the anti-infective agent comprises chlorhexidine.

7. The method of claim 2, wherein the temperature of the loading solution is maintained at greater than about 35° C. for at least 12 hours while in contact with wall.

8. The method of claim 2, wherein the medical catheter or tube is a urinary catheter, medical drainage tube, feeding tube, a trachea tube, an intravenous catheter, a central venous catheters, an arterial catheter, a peripherally inserted central catheter, an umbilical (arterial or venous) catheters, a gastric tube, a uterine tube, a chest tube, a peritoneal catheter, a renal catheter, a dialysis catheter, or a tissue drainage tube.

9. The method of claim 2, wherein the metical catheter or tube is a urinary catheter.

10. The system of claim 1, wherein the wall concentration of the local anesthetic agent is at least 5 mg/cm$^2$.

11. The system of claim 1, wherein the wall concentration of the local anesthetic agent is at least 10 mg/cm$^2$.

12. The system of claim 1, wherein the wall concentration of the local anesthetic agent is at least 15 mg/cm$^2$.

13. The system of claim 12, wherein the local anesthetic agent comprises lidocaine.

14. The system of claim 13, wherein the lidocaine is absorbed into the wall material at a wall concentration of at least 1 mg/cm$^2$.

15. The system of claim 13, wherein the lidocaine is absorbed into the wall material at a wall concentration of at least 5 mg/cm$^2$.

16. The system of claim 1, wherein the loading solution further comprises an anti-infective agent, and the anti-infective agent is also absorbed into the wall material.

17. The system of claim 16, wherein the anti-infective agent comprises chlorhexidine.

18. The system of claim 1, wherein at least some wall area of the medical catheter or tube, when removed from the loading solution and submerged in a 0.9% sodium chloride in water solution, will release the local anesthetic at a rate greater than 10 mcg/hour/cm$^2$ continuously for at least 72 hours at 37° C.

19. The system of claim 1, wherein the local anesthetic in the wall material of the medical catheter or tube and the local anesthetic in the loading solution are in dynamic equilibrium.

20. The system of claim 1, wherein the medical catheter or tube is a urinary catheter.

21. The system of claim 1, wherein the medical catheter or tube is a medical drainage tube, feeding tube, a trachea tube, an intravenous catheter, a central venous catheters, an arterial catheter, a peripherally inserted central catheter, an umbilical (arterial or venous) catheters, a gastric tube, a uterine tube, a chest tube, a peritoneal catheter, a renal catheter, a dialysis catheter, or a tissue drainage tube.

22. The system of claim 1, wherein the pH of the loading solution is greater than about 7.0.

23. The system of claim 1, wherein the viscosity of the loading solution is greater than about 300 centipoise.

24. A urinary catheter system, comprising: a urinary catheter comprising wall material having an outer wall surface and an inner wall surface, a loading solution in which at least a portion of the outer wall surface has been submersed for at least 30 days, and lidocaine in the loading solution and absorbed into the wall material, wherein the pH of the loading solution is greater than about 7.0, wherein the viscosity of the loading solution is greater than about 300 centipoise, wherein at least one portion of the urinary catheter has a wall concentration of lidocaine of at least 1 mg/cm$^2$, and wherein a volume of the loading solution is in the range of 0.2 to 10 mL for each cm$^2$ of the outer wall surface area submersed in the loading solution.

25. The system of claim 24, wherein the wall concentration of the local anesthetic agent is at least 5 mg/cm$^2$.

26. The system of claim 24, wherein the wall concentration of the local anesthetic agent is at least 10 mg/cm$^2$.

27. The system of claim 24, wherein the wall concentration of the local anesthetic agent is at least 15 mg/cm$^2$.

28. The system of claim 27, wherein the local anesthetic agent comprises lidocaine.

29. The system of claim 28, wherein the lidocaine is absorbed into the wall material at a wall concentration of at least 1 mg/cm$^2$.

30. The system of claim 28, wherein the lidocaine is absorbed into the wall material at a wall concentration of at least 5 mg/cm$^2$.

31. The system of claim 24, wherein the loading solution further comprises an anti-infective agent, and the anti-infective agent is also absorbed into the wall material.

32. The system of claim 31, wherein the anti-infective agent comprises chlorhexidine.

33. The system of claim 24, wherein at least some wall area of the urinary catheter, when removed from the loading solution and submerged in a 0.9% sodium chloride in water solution, will release the local anesthetic at a rate greater than 10 mcg/hour/cm$^2$ continuously for at least 72 hours at 37° C.

34. The system of claim 24, wherein the local anesthetic in the wall material of the urinary catheter and the local anesthetic in the loading solution are in dynamic equilibrium.

35. The system of claim 24, wherein the pH of the loading solution is greater than about 7.0.

36. The system of claim 24, wherein the viscosity of the loading solution is greater than about 300 centipoise.

* * * * *